(12) United States Patent
Griffin

(10) Patent No.: US 9,232,948 B2
(45) Date of Patent: Jan. 12, 2016

(54) CATHETER WITH DISTAL OCCLUSION APPARATUS

(75) Inventor: Stephen Griffin, San Jose, CA (US)

(73) Assignees: Stryker Corporation, Kalamazoo, MI (US); Stryker European Holdings I, LLC, Kalamazoo, MI (US)

(*) Notice: Subject to any disclaimer, the term of this patent is extended or adjusted under 35 U.S.C. 154(b) by 776 days.

(21) Appl. No.: 10/745,735

(22) Filed: Dec. 23, 2003

(65) Prior Publication Data

US 2005/0137622 A1    Jun. 23, 2005

(51) Int. Cl.
| | | |
|---|---|---|
| *A61M 29/00* | (2006.01) |
| *A61B 17/12* | (2006.01) |
| *A61B 17/22* | (2006.01) |
| *A61M 25/06* | (2006.01) |
| *A61M 25/10* | (2013.01) |

(52) U.S. Cl.
CPC ..... *A61B 17/12022* (2013.01); *A61B 17/12136* (2013.01); *A61B 17/12172* (2013.01); *A61B 2017/22067* (2013.01); *A61M 25/0662* (2013.01); *A61M 2025/1052* (2013.01)

(58) Field of Classification Search
CPC .................. A61B 17/12022; A61B 17/12136; A61B 17/12172; A61B 2017/22067; A61M 2025/1052; A61M 25/0662
USPC ................. 604/93.01, 96.01, 103.05, 103.07, 604/103.08, 103.09, 915–917, 921, 104, 604/107; 606/191–192, 194
See application file for complete search history.

(56) References Cited

U.S. PATENT DOCUMENTS

| | | |
|---|---|---|
| 3,044,468 A | 7/1962 | Birtwell |
| 3,087,492 A | 4/1963 | Garth |
| 3,190,291 A | 6/1965 | Foley |
| 3,192,949 A | 7/1965 | De See |
| 3,211,150 A | 10/1965 | Foderick |
| 3,331,371 A | 7/1967 | Rocchi et al. |
| 3,378,011 A | 4/1968 | Vitello |
| 3,379,197 A | 4/1968 | Hayes |
| 3,402,717 A | 9/1968 | Doherty |
| 3,402,718 A | 9/1968 | Doherty |
| 3,417,750 A | 12/1968 | Carson |
| 3,527,226 A | 9/1970 | Hakim |
| 3,602,226 A | 8/1971 | Ericson |
| 3,675,658 A | 7/1972 | Taylor |
| 3,726,282 A | 4/1973 | Patel |
| 3,726,283 A | 4/1973 | Dye et al. |
| 3,742,960 A | 7/1973 | Dye et al. |

(Continued)

FOREIGN PATENT DOCUMENTS

| | | |
|---|---|---|
| DE | 36 25 871 A1 | 2/1988 |
| EP | 0 272 112 A2 | 6/1988 |

(Continued)

*Primary Examiner* — Jason Flick
(74) *Attorney, Agent, or Firm* — Vista IP Law Group LLP

(57) ABSTRACT

Catheters such as guide catheters can be configured to provide distal occlusion, while still providing sufficient interior lumen space for device delivery. Such catheters can also provide a desired level of flexibility, yet can include sufficient column support. A catheter can include an elongate shaft having a distal region, a proximal region and a lumen extending therebetween. A distal occlusion member can be disposed over a portion of the distal region of the elongate shaft and an occlusion activating member can be disposed over the elongate shaft.

4 Claims, 6 Drawing Sheets

(56) References Cited

U.S. PATENT DOCUMENTS

| | | |
|---|---|---|
| 3,799,171 A | 3/1974 | Patel |
| 3,908,267 A | 9/1975 | Loyd et al. |
| 3,982,544 A | 9/1976 | Dyck |
| 3,985,139 A | 10/1976 | Penar |
| 4,026,298 A | 5/1977 | Grausz |
| 4,028,037 A | 6/1977 | Dawson |
| 4,088,135 A | 5/1978 | O'Neill |
| 4,205,683 A | 6/1980 | O'Neill |
| 4,205,691 A | 6/1980 | Patel |
| 4,318,410 A | 3/1982 | Chin |
| 4,323,071 A | 4/1982 | Simpson et al. |
| 4,333,452 A | 6/1982 | Au |
| 4,411,055 A | 10/1983 | Simpson et al. |
| 4,413,989 A | 11/1983 | Schjeldahl et al. |
| 4,445,892 A | 5/1984 | Hussein et al. |
| 4,506,691 A | 3/1985 | Tseo |
| 4,517,979 A | 5/1985 | Pecenka |
| 4,545,367 A | 10/1985 | Tucci |
| 4,549,879 A | 10/1985 | Groshong et al. |
| 4,564,014 A | 1/1986 | Fogarty et al. |
| 4,582,181 A | 4/1986 | Samson |
| 4,597,755 A | 7/1986 | Samson et al. |
| 4,606,347 A | 8/1986 | Fogarty et al. |
| 4,614,188 A | 9/1986 | Bazell et al. |
| 4,646,742 A | 3/1987 | Packard et al. |
| 4,684,363 A | 8/1987 | Ari et al. |
| 4,696,304 A | 9/1987 | Chin |
| 4,710,168 A | 12/1987 | Schwab et al. |
| 4,715,378 A | 12/1987 | Pope, Jr. et al. |
| 4,723,547 A | 2/1988 | Kullas et al. |
| 4,748,982 A | 6/1988 | Hozewski et al. |
| 4,762,129 A | 8/1988 | Bonzel |
| 4,779,611 A | 10/1988 | Grookrs et al. |
| 4,793,351 A | 12/1988 | Landman et al. |
| 4,800,109 A | 1/1989 | Washizu |
| 4,811,737 A | 3/1989 | Rydell |
| 4,848,344 A | 7/1989 | Sos et al. |
| 4,856,510 A | 8/1989 | Kowalewski |
| 4,902,095 A | 2/1990 | Baker et al. |
| 4,921,483 A | 5/1990 | Wijay et al. |
| 4,923,498 A | 5/1990 | Gregory |
| 4,930,341 A | 6/1990 | Euteneuer |
| 4,932,959 A | 6/1990 | Horzewski et al. |
| 4,943,278 A | 7/1990 | Euteneuer et al. |
| 4,968,306 A | 11/1990 | Huss et al. |
| 4,998,923 A | 3/1991 | Samson et al. |
| 5,015,233 A | 5/1991 | McGough et al. |
| 5,022,422 A | 6/1991 | di Palma |
| 5,035,705 A | 7/1991 | Burns |
| 5,059,176 A | 10/1991 | Winters |
| 5,061,240 A | 10/1991 | Cherian |
| 5,085,636 A | 2/1992 | Burns |
| 5,100,385 A | 3/1992 | Bromander |
| 4,813,934 B1 | 5/1992 | Engelson et al. |
| 5,114,398 A | 5/1992 | Trick et al. |
| 5,120,323 A | 6/1992 | Shockey et al. |
| 5,160,321 A | 11/1992 | Sahota |
| 5,167,239 A | 12/1992 | Cohen et al. |
| 5,171,221 A | 12/1992 | Samson |
| 5,180,364 A | 1/1993 | Ginsburg |
| 5,180,367 A | 1/1993 | Kontos et al. |
| 5,209,728 A | 5/1993 | Kraus et al. |
| 5,217,434 A | 6/1993 | Arney |
| 5,217,474 A | 6/1993 | Zacca et al. |
| 5,224,933 A | 7/1993 | Bromander |
| 5,238,004 A | 8/1993 | Sahatjan et al. |
| 5,246,420 A | 9/1993 | Kraus et al. |
| 5,259,839 A | 11/1993 | Burns |
| 5,297,546 A | 3/1994 | Spofford et al. |
| 5,304,198 A | 4/1994 | Samson |
| 5,306,246 A | 4/1994 | Sahatjian |
| 5,320,604 A | 6/1994 | Walker et al. |
| 5,324,255 A | 6/1994 | Passafaro et al. |
| 5,334,153 A | 8/1994 | McIntyre et al. |
| 5,336,174 A | 8/1994 | Daoud et al. |
| 5,338,301 A | 8/1994 | Diaz |
| 5,378,238 A | 1/1995 | Peters et al. |
| 5,423,742 A | 6/1995 | Theron |
| 5,443,457 A | 8/1995 | Ginn et al. |
| 5,449,343 A | 9/1995 | Samson et al. |
| 5,456,667 A * | 10/1995 | Ham et al. ............... 604/107 |
| 5,490,859 A | 2/1996 | Mische et al. |
| RE35,176 E | 3/1996 | Powell |
| 5,496,310 A | 3/1996 | Exonde et al. |
| 5,501,694 A | 3/1996 | Ressemann et al. |
| 5,536,252 A | 7/1996 | Imran et al. |
| 5,540,707 A | 7/1996 | Ressemann et al. |
| 5,545,133 A | 8/1996 | Burns et al. |
| 5,695,468 A | 12/1997 | Lafontaine et al. |
| 5,709,653 A | 1/1998 | Leone |
| 5,718,683 A | 2/1998 | Ressemann et al. |
| 5,743,875 A | 4/1998 | Sirhan et al. |
| 5,772,642 A | 6/1998 | Ciamacco, Jr. et al. |
| 5,785,685 A | 7/1998 | Kugler et al. |
| 5,807,328 A | 9/1998 | Briscoe |
| 5,807,330 A | 9/1998 | Teitelbaum |
| 5,814,016 A | 9/1998 | Valley et al. |
| 5,833,644 A | 11/1998 | Zadno-Azizi et al. |
| 5,833,650 A | 11/1998 | Imran |
| 5,836,924 A | 11/1998 | Kelliher et al. |
| 5,897,567 A | 4/1999 | Ressemann et al. |
| 5,916,194 A | 6/1999 | Jacobsen et al. |
| 5,925,016 A | 7/1999 | Chornenky et al. |
| 5,944,716 A | 8/1999 | Hektner |
| 5,968,064 A | 10/1999 | Selmon et al. |
| 5,972,019 A | 10/1999 | Engelson et al. |
| 6,017,323 A | 1/2000 | Chee |
| 6,027,476 A | 2/2000 | Sterman et al. |
| 6,042,563 A | 3/2000 | Morejohn |
| 6,050,972 A | 4/2000 | Zadno-Azizi et al. |
| 6,056,721 A | 5/2000 | Shulze |
| 6,071,273 A | 6/2000 | Euteneuer et al. |
| 6,090,083 A | 7/2000 | Sell et al. |
| 6,102,891 A | 8/2000 | van Erp |
| 6,102,931 A | 8/2000 | Thorton |
| 6,126,685 A * | 10/2000 | Lenker et al. ............. 623/1.11 |
| 6,176,843 B1 | 1/2001 | DiCaprio et al. |
| 6,231,588 B1 | 5/2001 | Zadno-Azizi |
| 6,260,552 B1 | 7/2001 | Mortiter et al. |
| 6,319,228 B1 | 11/2001 | Kastenhofer |
| 6,321,407 B1 | 11/2001 | Weihrauch |
| 6,350,252 B2 * | 2/2002 | Ray et al. ................. 604/107 |
| 6,355,014 B1 | 3/2002 | Zadno-Azizi et al. |
| 6,475,185 B1 | 11/2002 | Rauker et al. |
| 6,508,803 B1 | 1/2003 | Horikawa |
| 6,582,448 B1 | 6/2003 | Boyle et al. |
| 6,626,861 B1 * | 9/2003 | Hart et al. ................ 604/96.01 |
| 6,689,098 B2 | 2/2004 | Rauker et al. |
| 6,764,505 B2 * | 7/2004 | McGuckin et al. ......... 604/104 |
| 2001/0018596 A1 | 8/2001 | Selmon et al. |
| 2001/0041858 A1 * | 11/2001 | Ray et al. ................. 604/93.01 |
| 2001/0041862 A1 | 11/2001 | Glickman |
| 2002/0103473 A1 | 8/2002 | Roychowdhury et al. |
| 2003/0163114 A1 | 8/2003 | Gershowitz |

FOREIGN PATENT DOCUMENTS

| | | |
|---|---|---|
| EP | 0 402 467 A1 | 12/1990 |
| EP | 0 547 358 A2 | 6/1993 |
| EP | 0 547 358 A3 | 6/1993 |
| EP | 0 569 030 A1 | 11/1993 |
| EP | 0 710 490 A2 | 5/1996 |
| EP | 0 710 490 A3 | 5/1996 |
| EP | 0 769 307 A2 | 4/1997 |
| GB | 2 139 725 A | 11/1984 |
| GB | 2 209 121 A | 5/1989 |
| GB | 2 277 875 A | 11/1994 |
| JP | 56-152655 A | 11/1981 |
| JP | 1-232927 A | 9/1989 |
| WO | WO 92/13589 A1 | 8/1992 |
| WO | WO 93/17750 | 9/1993 |

(56) References Cited

FOREIGN PATENT DOCUMENTS

| WO | WO 97/44082 A2 | 11/1997 |
| WO | WO 97/44085 A2 | 11/1997 |
| WO | WO 98/38930 A1 | 9/1998 |
| WO | WO 99/26692 A1 | 6/1999 |
| WO | WO 99/42161 A2 | 8/1999 |
| WO | WO 99/45835 A2 | 9/1999 |

* cited by examiner

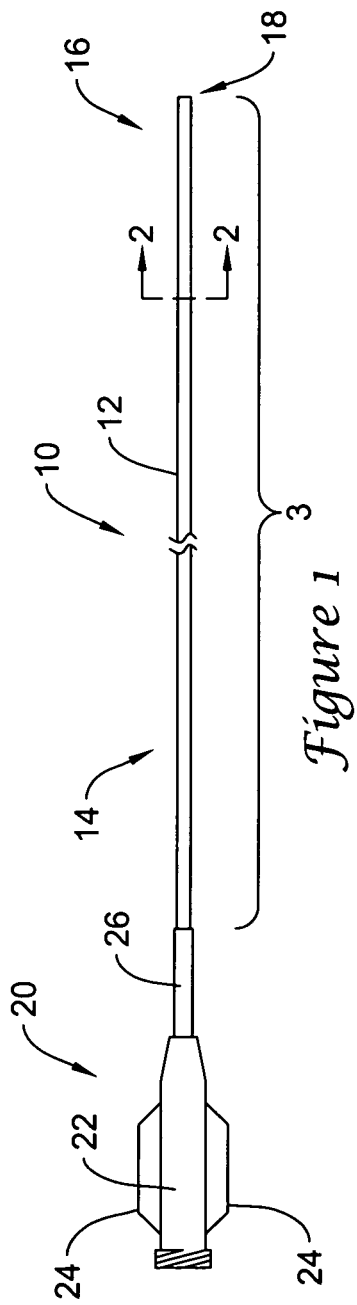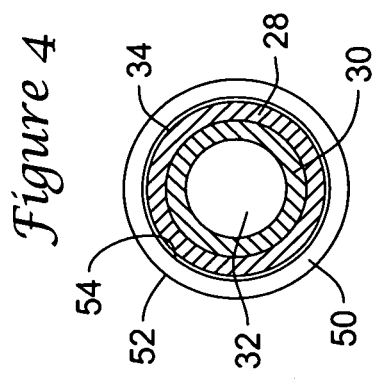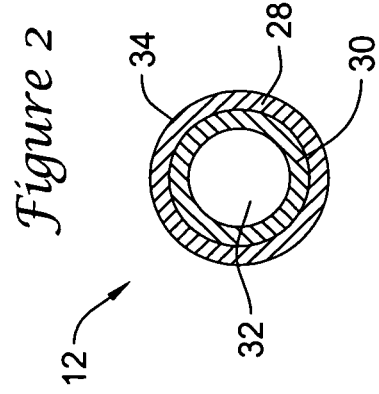

CATHETER WITH DISTAL OCCLUSION APPARATUS

TECHNICAL FIELD

The invention relates generally to catheters and more specifically to catheters that include distal occlusion means.

BACKGROUND OF THE INVENTION

Catheters such as guide catheters can be subject to a number of often conflicting performance requirements such as flexibility, strength, minimized exterior diameter, maximized interior diameter, and the like. In particular, there can be a balance between a need for flexibility and a need for strength or column support. If a catheter is sufficiently flexible to reach and pass through tortuous vasculature, the catheter may lack sufficient column strength to remain in position while, for example, subsequent treatment devices are advanced through the catheter.

Some medical procedures require a method of occluding blood flow distally of a treatment site, while other procedures benefit from occluding blood flow proximally of a treatment site. While a balloon catheter can be used to occlude blood flow, inclusion of a balloon catheter requires either a separate lumen through a guide catheter or a substantial amount of the lumen space within the guide catheter.

A need remains for a catheter such as a guide catheter that can provide desired strength versus flexibility characteristics. A need remains for a catheter such as a guide catheter that can occlude blood flow without sacrificing the interior lumen space otherwise required by a balloon catheter.

SUMMARY OF THE INVENTION

The invention is directed to catheters such as guide catheters configured for providing distal occlusion, while still providing sufficient interior lumen space for device delivery. The invention is directed to catheters such as guide catheters that also provide a desired level of flexibility, yet can include sufficient column support.

Accordingly, an example embodiment of the invention can be found in a catheter that includes an elongate shaft having a distal region, a proximal region and a lumen extending therebetween. Distal occlusion means are disposed over a portion of the distal region of the elongate shaft and occlusion activating means are disposed over the elongate shaft.

Another example embodiment of the invention can be found in a guide catheter assembly having a distal region and a proximal region. An elongate shaft extends from the distal region to the proximal region and defines a lumen extending therebetween. An outer member is slidably disposed over an outer surface of the elongate shaft. An expandable member is disposed over the outer surface of the elongate shaft such that a distal end of the outer member is proximate a proximal end of the expandable member. A stop is disposed on the elongate shaft in order to limit distal travel of the expandable member. A distal end of the expandable member contacts the stop.

Another example embodiment of the invention can be found in a method of deploying a treatment device within a patient's vasculature. A distal occlusion device is provided that has a distal region, a proximal region and a lumen extending therebetween. The distal occlusion device includes an elongate shaft extending between the distal region and the proximal region, an outer tube disposed over a portion of the elongate shaft, and an expandable member disposed over the elongate shaft.

The distal occlusion device is advanced through the vasculature, and the outer tube is advanced distally to expand the expandable member to engage the expandable ember and to transform the expandable member from an initial collapsed configuration to an expanded or engaged configuration. The treatment device is advanced through the lumen.

BRIEF DESCRIPTION OF THE DRAWINGS

The invention may be more completely understood in consideration of the following detailed description of various embodiments of the invention in connection with the accompanying drawings, in which:

FIG. 1 is a side elevation view of an intravascular catheter in accordance with an embodiment of the invention;

FIG. 2 is a cross-sectional view taken along line 2-2 of FIG. 1;

FIG. 4 is a cross-sectional view of the catheter of FIG. 3 at line 4-4;

DETAILED DESCRIPTION OF PREFERRED EMBODIMENTS

Figure 3:
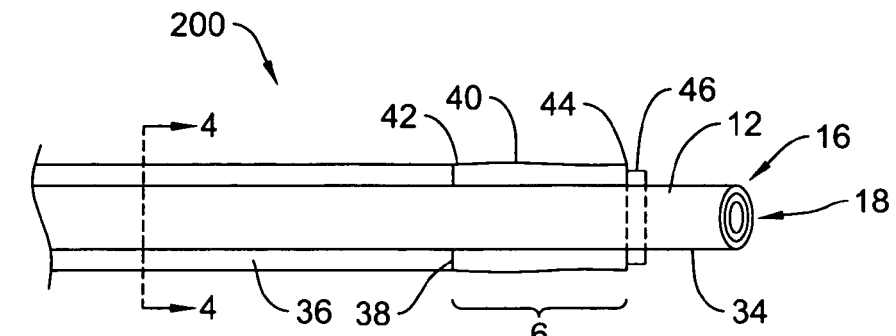
FIG. 3 is a partially sectioned view of a portion of a catheter assembly including the intravascular catheter of FIG. 1 with an outer member and an expandable member positioned over the intravascular catheter.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a plan view of a catheter 10 in accordance with an embodiment of the invention. The catheter 10 can be one of a variety of different catheters, but is preferably an intravascular catheter. Examples of intravascular catheters include balloon catheters, atherectomy catheters, drug delivery catheters, diagnostic catheters and guide catheters. As illustrated, FIG. 1 portrays a guide catheter, but the invention is not limited to such. Except as described herein, the intravascular catheter 10 can be manufactured using conventional techniques and materials.

The intravascular catheter 10 can be sized in accordance with its intended use. The catheter 10 can have a length that is in the range of about 50 centimeters to about 100 centimeters and can have a diameter that is in the range of about 4 F (French) to about 9 F.

In the illustrated embodiment, the intravascular catheter 10 includes an elongate shaft 12 that has a proximal region 14, a distal region 16 and a distal end 18. A hub and strain relief assembly 20 can be connected to the proximal region 14 of the elongate shaft 12. The hub and strain relief assembly 20 includes a main body portion 22, a pair of flanges 24 designed to improve gripping, and a strain relief 26 that is intended to reduce kinking. The hub and strain relief assembly 20 can be of conventional design and can be attached using conventional techniques.

FIG. 2 is a cross-sectional view of the elongate shaft 12, taken along line 2-2 of FIG. 1. The elongate shaft 12 includes an outer layer 28 and an inner layer 30. Each of the outer layer 28 and the inner layer 30 can extend from the proximal region 14 of the elongate shaft 12 to the distal region 16 of the elongate shaft 12. The inner layer 30 defines a lumen 32 that extends through the elongate shaft 12.

In some embodiments, the elongate shaft 12 can optionally include a reinforcing braid or ribbon layer to increase particular properties such as kink resistance. If a reinforcing braid or ribbon layer is included, it can be positioned between the outer layer 28 and the inner layer 30.

In some embodiments (not illustrated), the elongate shaft 12 can include one or more shaft segments having varying degrees of flexibility. For example, the elongate shaft 12 can include a proximal segment, an intermediate segment and a distal segment. In some embodiments, the elongate shaft 12 can also include a distal tip segment that can be formed from a softer, more flexible polymer. The elongate shaft 12 can include more than three segments, or the elongate shaft 12 can include fewer than three segments.

If the elongate shaft 12 has, for example, three segments, such as a proximal segment, an intermediate segment and a distal segment, each segment can include an inner layer 30 that is the same for each segment and an outer layer that becomes increasingly more flexible with proximity to the distal end 18 of the elongate shaft 12. For example, the proximal segment can have an outer layer that is formed from a polymer having a hardness of 72 D (Durometer), the intermediate segment can have an outer layer that is formed from a polymer having a hardness of 68 D and the distal segment can be formed from a polymer having a hardness of 46 D.

If the elongate shaft 12 has three segments, each of the segments can be sized in accordance with the intended function of the resulting catheter 10. For example, the proximal segment can have a length of about 35 inches, the intermediate segment can have a length that is in the range of about 2 inches to about 3 inches, and the distal segment can have a length that is in the range of about 1 inch to about 1.25 inches.

The inner layer 30 can be a uniform material and can define a lumen 32 that can run the entire length of the elongate shaft 12 and that is in fluid communication with a lumen (not illustrated) extending through the hub assembly 20. The lumen 32 defined by the inner layer 30 can provide passage to a variety of different medical devices, and thus, the inner layer 30 can include, be formed from or coated with a lubricious material to reduce friction within the lumen 32. An exemplary material is polytetrafluoroethylene (PTFE), better known as TEFLON®. The inner layer 30 can be dimensioned to define a lumen 32 having an appropriate inner diameter to accommodate its intended use. In some embodiments, the inner layer 30 can define a lumen 32 having a diameter of about 0.058 inches and the inner layer 30 can have a wall thickness of about 0.001 inches.

The outer layer 28 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX®), silicones, and co-polymers. The outer layer 28 can be a single polymer, multiple layers, or a blend of polymers. By employing careful selection of materials and processing techniques, thermoplastic, solvent soluble, and thermosetting variants of these materials can be employed to achieve the desired results.

In particular embodiments, a thermoplastic polymer such as a co-polyester thermoplastic elastomer such as that available commercially under the ARNITEL® name can be used. The outer layer 28 can have an inner diameter that is about equal to the outer diameter of the inner layer 30. The outer layer 28 defines an outer surface 34.

In some embodiments, the outer layer 28 can have an inner diameter in the range of about 0.0600 inches to about 0.0618 inches and an outer diameter in the range of about 0.0675 inches to about 0.0690 inches. Part or all of the outer layer 28 can include materials added to increase the radiopacity of the outer layer 28, such as 50% bismuth subcarbonate.

Turning to FIG. 3, a portion of the elongate shaft 12 is illustrated with additional elements disposed over the outer surface 34 of the elongate shaft 12. An occlusion activating means, illustrated as an outer member 36 having a distal end 38 is slidingly disposed over the elongate shaft 12. An occlusion means, illustrated as an expandable member 40 having a proximal end 42 and a distal end 44 is also disposed over the elongate shaft 12. A distal stop 46 is secured to the outer surface 34 of the elongate shaft 12. In combination, the elongate shaft 12, outer member 36, expandable member 40 and distal stop 46 form a catheter assembly 200.

In some embodiments, the outer member 36 can be positioned such that its distal end 38 is close to or even in contact with the proximal end 42 of the expandable member 40. In some embodiments, the distal stop 46 limits distal travel of the expandable member 40 and is positioned within the distal region 16 of the elongate shaft 12.

As illustrated, for example, in FIG. 4, which is a cross-section taken along line 4-4 of FIG. 3, the outer member 36 can be a single layer 50 having a lumen therethrough that is sized to accommodate the outer surface 34 of the elongate shaft 12. In some embodiments, the outer member 36 can have an outer diameter that is in the range of about 0.065 inches to about 0.13 inches and an inner diameter that is in the range of about 0.050 inches to about 0.12 inches. The outer member 36 can have an overall length that is in the range of about 50 cm to about 150 cm.

The single layer 50 has an outer surface 52 and an inner surface 54. The outer member 36 can be formed of any suitable material such as a polymeric material. Polymers with low durometer or hardness can provide increased flexibility, while polymers with high durometer or hardness can provide increased stiffness. In some embodiments, the outer member 36 can be formed of a material that will provide the outer member 36 with characteristics useful in providing column support to the elongate shaft 12 when the outer member 36 is deployed thereon.

In some embodiments, the polymer material used is a thermoplastic polymer material. Some examples of some suitable materials include those discussed previously with respect to the outer layer 28 of the elongate shaft 12. By employing careful selection of materials and processing techniques, thermoplastic, solvent soluble, and thermosetting variants of these materials can be employed to achieve the desired results.

In the illustrated embodiment in which the outer member 36 is a single layer 50, the inner surface 54 of the outer member 36 can be coated with a lubricious material to reduce friction between the inner surface 54 of the outer member 36 and the outer surface 34 of the elongate shaft 12. An exemplary material is polytetrafluoroethylene (PTFE), better known as TEFLON®.

In some embodiments (not illustrated), the outer member 36 can be formed having two or more layers. In such embodiments, the outer member 36 can have an inner layer that includes, is coated with, or formed from TEFLON®. The outer layer can be formed of any suitable polymer such as those discussed with respect to the outer layer 28 of the elongate shaft 12.

Figure 5:
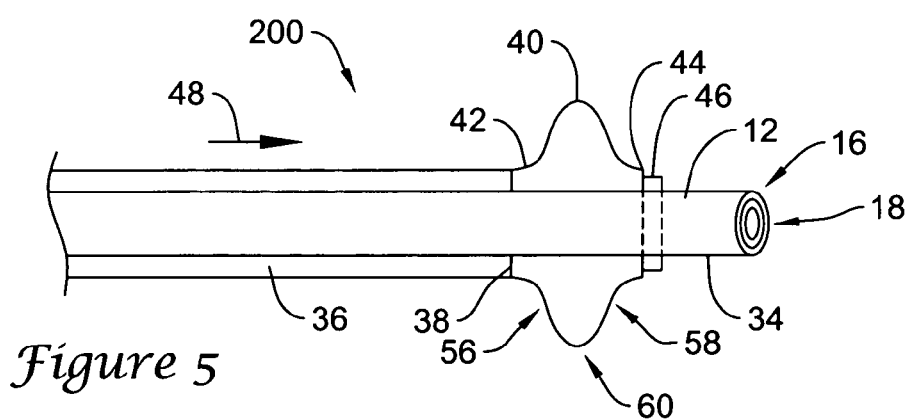
FIG. 5 is a partially-sectioned view of FIG. 3, showing the expandable member in an expanded configuration.

The expandable member 40 is moveable between a collapsed configuration, as seen in FIG. 3, and an expanded configuration as seen in FIG. 5. In the collapsed configuration, the expandable member 40 has a first length and a first diameter. In the expanded configuration, the expandable member 40 has a second length and a second diameter. By comparing FIG. 3 to FIG. 5, it is clear that the first length of the expandable member is greater than the second length, while the second diameter is greater than the first diameter.

The expandable member 40 can be sized as appropriate to fit over the outer surface 34 of the elongate shaft 12, as well as to nearly or completely occlude a particular vasculature in which the expandable member 40 will be used. In some embodiments, the expandable member 40 can have a first length (collapsed configuration) that is in the range of about 1 cm to about 2 cm and a second length (expanded configuration) that is in the range of about 0.5 cm to about 1.0 cm. The expandable member 40 can have a first diameter (collapsed configuration) that is in the range of about 0.065 inches to about 0.13 inches and a second diameter (expanded configuration) that is in the range of about 1 mm to about 1.5 cm.

The distal stop 46 can be removably or permanently secured to the outer surface 34 of the elongate shaft 12. The distal stop 46 can be formed from any suitable material that can be adhered or otherwise secured to the outer surface 34 of the elongate shaft and the distal stop 46 can have any suitable configuration or structure that is adapted to limit distal travel of the expandable member 40.

In some embodiments, the distal stop 46 can include a metallic or polymeric ring that is bonded to the outer surface 34 of the elongate shaft 12. In other embodiments, the distal stop 46 can be formed by creating a narrow band of molten or nearly molten material at least partway around the circumference of the outer surface 34 of the elongate shaft 12. In some embodiments, the distal stop 46 can be a metal clamp secured to the outer surface 34 of the elongate shaft 12.

With respect to FIG. 5, in some embodiments, moving the outer member 36 distally, as evidenced by an arrow 48, causes the proximal end 42 of the expandable member 40 to move distally. As the distal end 44 of the expandable member 40 is held in place by the distal stop 46, moving the outer member 36 distally causes the proximal end 42 of the expandable member 40 to move closer to the distal end 44 thereof.

The expandable member 40 can be considered as having a proximal portion 56, a distal portion 58 and an intermediate portion 60. As the distal end 44 of the expandable member 40 moves distally and closer to the proximal end 42 thereof, at least the intermediate portion 60 moves radially outward.

Figure 6:
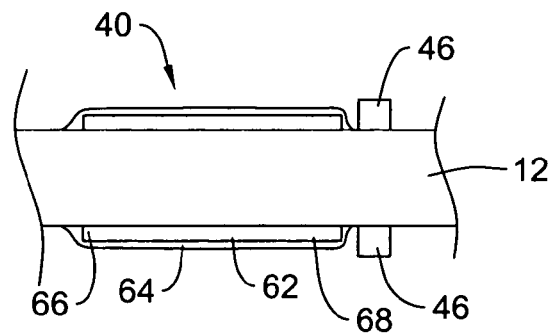
FIG. 6 is a partially-sectioned view of a portion of FIG. 3, showing the expandable member in greater detail.

FIGS. 6 through 10 describe the expandable member 40 in greater detail. FIG. 6 is a partially-sectioned view of a portion of FIG. 3 in which expandable member 40 is depicted as a cylindrical member 62 having an overlaying polymer sheath 64. The expandable member 40 has a proximal end 66 and a distal end 68. In some embodiments, as illustrated, the polymer sheath 64 can extend proximally a slight distance beyond the proximal end 66 and can extend distally a slight distance beyond the distal end 68 of the expandable member 40. In other embodiments, the polymer sheath 64 can extend only to or approximately to the proximal end 66 and the distal end 68 of the expandable member 40. The polymer sheath 64 can have a length that is in the range of about 1 cm to about 2 cm and an average thickness that is in the range of about 0.001 inches to about 0.002 inches.

The polymer sheath 64 can be formed of any suitable polymer that is sufficiently elastic to move with the cylindrical member 62 as the expandable member 40 moves between its collapsed and expanded configurations. In some embodiments, the polymer sheath 64 can be formed of a urethane polymer or a Chronoprene™ thermoplastic rubber elastomer available from Carditech International, Inc.

The cylindrical member 62 can be formed of materials such as metals, metal alloys, polymers, metal-polymer composites, or other suitable materials, and the like. Some examples of some suitable materials can include stainless steels (e.g., 304v stainless steel), nickel-titanium alloys (e.g., nitinol such as super elastic or linear elastic nitinol), nickel-chromium alloys, nickel-chromium-iron alloys, cobalt alloys, nickel, titanium, platinum, or alternatively, a polymer material such as a high performance polymer, or other suitable materials, and the like.

In some embodiments, the cylindrical member 62 can be formed of a shape memory material such as a nickel-titanium alloy. Nitinol is an exemplary shape memory material.

Within the family of commercially available nitinol alloy, is a category designated "linear elastic" which, although similar in chemistry to conventional shape memory and superelastic varieties, exhibits distinct and useful mechanical properties. By skilled applications of cold work, directional stress, and heat treatment, the tube is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

For example, in some embodiments, there is no martensite/austenite phase changes detectable by DSC and DMTA analysis in the range of about −60° C. to about 120° C. The mechanical bending properties of such material are, therefore, generally inert to the effect of temperature over this very broad range of temperature. In some particular embodiments, the mechanical properties of the alloy at ambient or room temperature are substantially the same as the mechanical properties at body temperature.

In some embodiments, the linear elastic nickel-titanium alloy is in the range of about 50 to about 60 weight percent nickel, with the remainder being essentially titanium. In some particular embodiments, the composition is in the range of about 54 to about 57 weight percent nickel. One example of a suitable nickel-titanium alloy is FHP-NT alloy commercially available from Furukawa Techno Material Co., of Kanagawa, Japan. Some examples of nickel-titanium alloys include those disclosed in U.S. Pat. Nos. 5,238,004 and 6,508,803, which are incorporated herein by reference.

Figure 7:
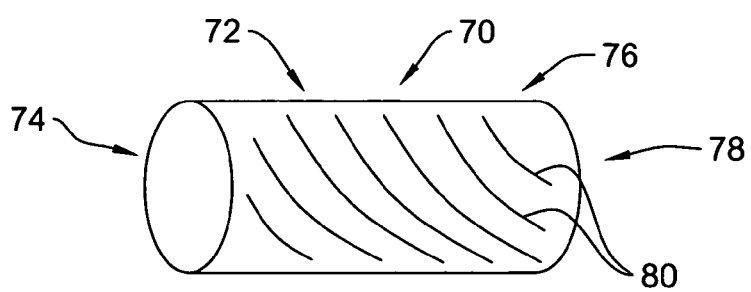
FIG. 7 is a side elevation view of a cylinder in accordance with an embodiment of the invention, seen in a collapsed configuration.

FIGS. 7 through 10 illustrate particular embodiments of cylindrical members. FIG. 7 illustrates a cylindrical member 70 having a proximal region 72, a proximal end 74, a distal region 76 and a distal end 78. A plurality of spirally aligned cuts 80 extend at least from the proximal region 72 to the distal region 76. In some embodiments, the spirally aligned cuts 80 extend from the proximal end 74 to the distal end 78. The spirally aligned cuts 80 can be formed in any suitable manner, such as by laser cutting. Each of the spirally aligned cuts 80 can extend completely through the cylindrical member 70 in a radial direction and can have a width that is in the range of about 0.0005 inches to about 0.1 inches.

Figure 8:
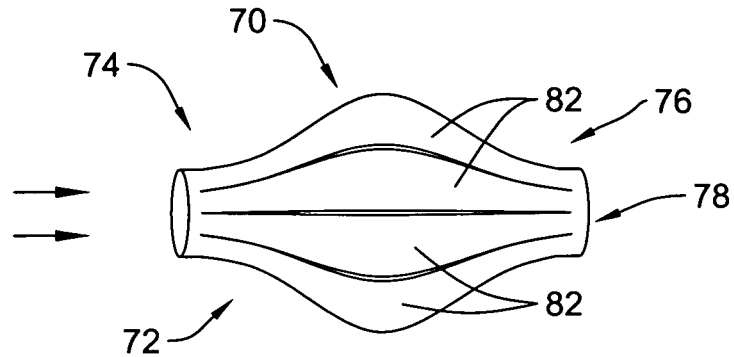
FIG. 8 is a side elevation view of the cylinder of FIG. 7, shown in an expanded configuration.

In FIG. 8, the cylindrical member 70 of FIG. 7 has been moved into its engaged configuration. As the outer member 36 moves distally and forces the proximal end 74 of the cylindrical member 70 to move distally toward the distal end 78 thereof, the spirally aligned cuts 80 can cause the proximal region 72 of the cylindrical member 70 to rotate with respect to the distal region 76. As the cylindrical member 70 opens up, a plurality of struts 82 representing the portions of the cylindrical member 70 positioned between adjacent spirally aligned cuts 80 will move radially outward.

Figure 9:
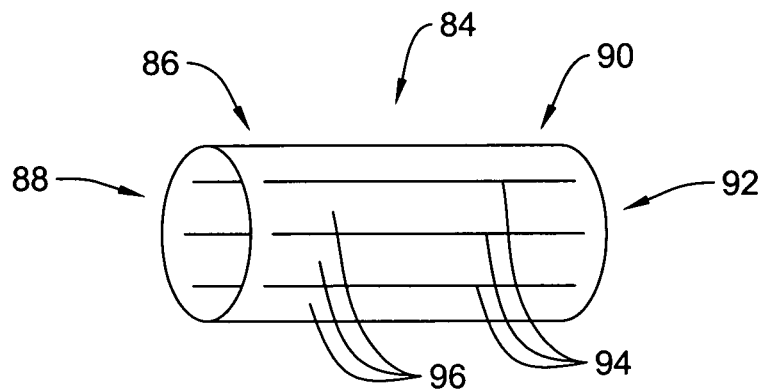
FIG. 9 is a side elevation view of a cylinder in accordance with another embodiment of the invention, seen in a collapsed configuration.

Turning to FIG. 9, another embodiment of a cylindrical member is shown. FIG. 9 illustrates a cylindrical member 84 having a proximal region 86, a proximal end 88, a distal region 90 and a distal end 92. A plurality of axially aligned cuts 94 extend at least from the proximal region 86 to the distal region 90. In some embodiments, the axially aligned cuts 94 extend from the proximal end 88 to the distal end 92. The axially aligned cuts 94 can be formed in any suitable manner, such as by laser cutting. Each of the axially aligned cuts 94 can extend completely through the cylindrical member 84 in a radial direction and can have a width that is in the range of about 0.0005 inches to about 0.1 inches.

Figure 10:
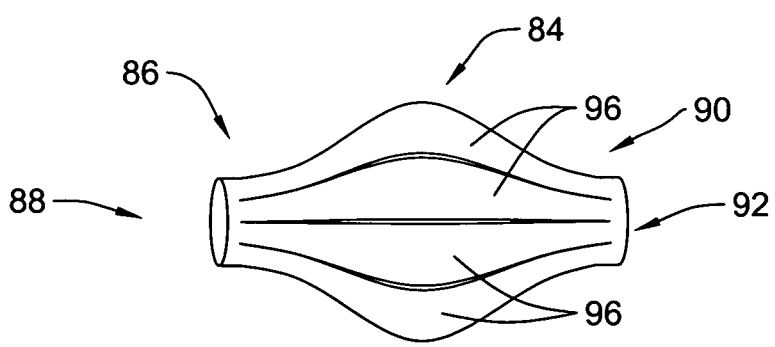
FIG. 10 is a side elevation view of the cylinder of FIG. 9, shown in an expanded configuration.

In FIG. 10, the cylindrical member 84 of FIG. 9 has been moved into its engaged configuration. As the outer member 36 moves distally and forces the proximal end 88 of the cylindrical member 84 to move distally toward the distal end 92 thereof, the axially aligned cuts 94 permit the proximal region 86 of the cylindrical member 84 to remain rotationally stationary with respect to the distal region 90. As the cylindrical member 70 opens up, a plurality of struts 96 representing the portions of the cylindrical member 84 positioned between adjacent axially aligned cuts 94 will move radially outward.

Figure 11:
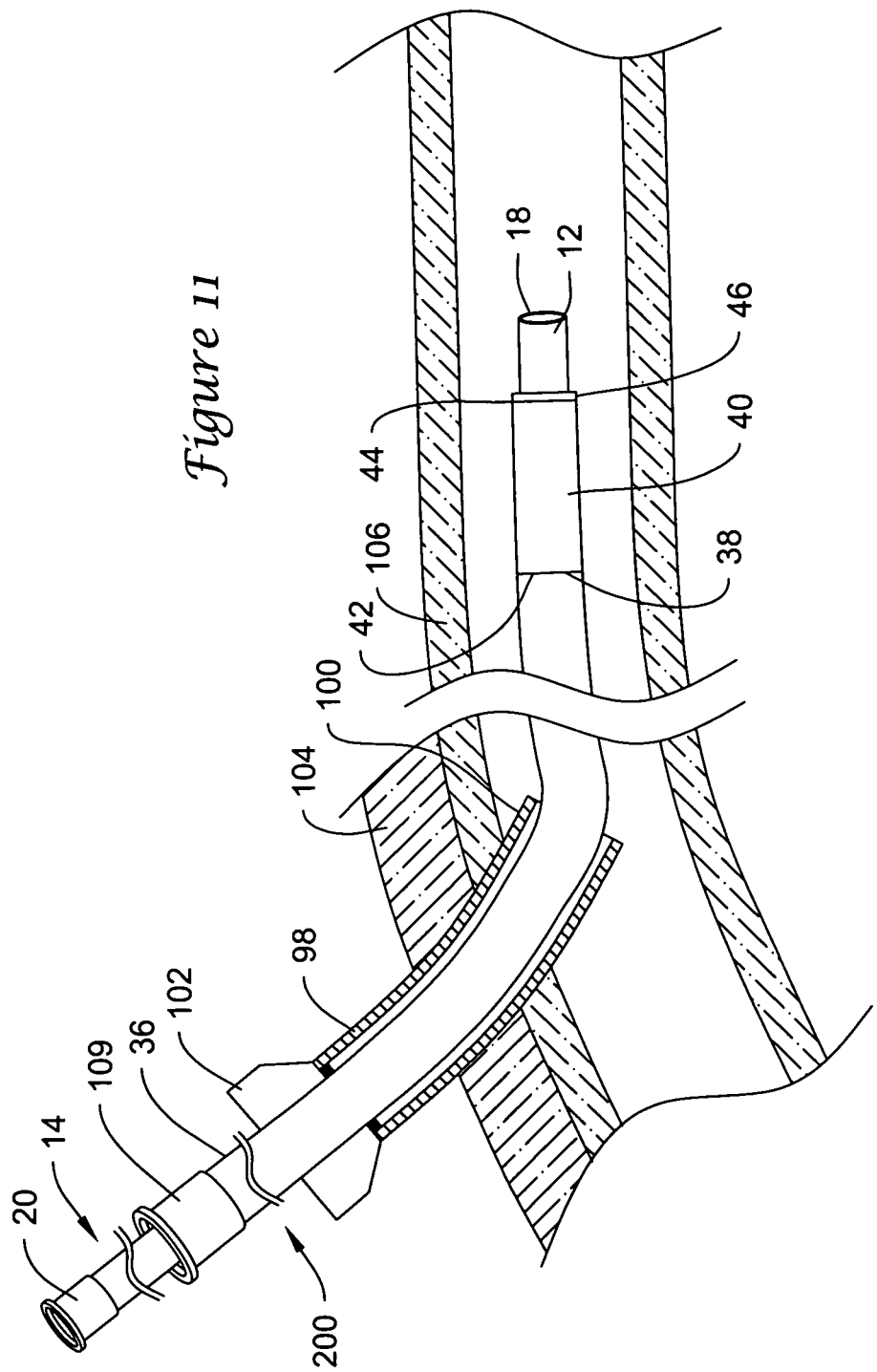
FIG. 11 is a partially-sectioned view of the catheter of FIG. 3, shown advanced into a patient's vasculature, the expandable member shown in its collapsed configuration.
Figure 12:
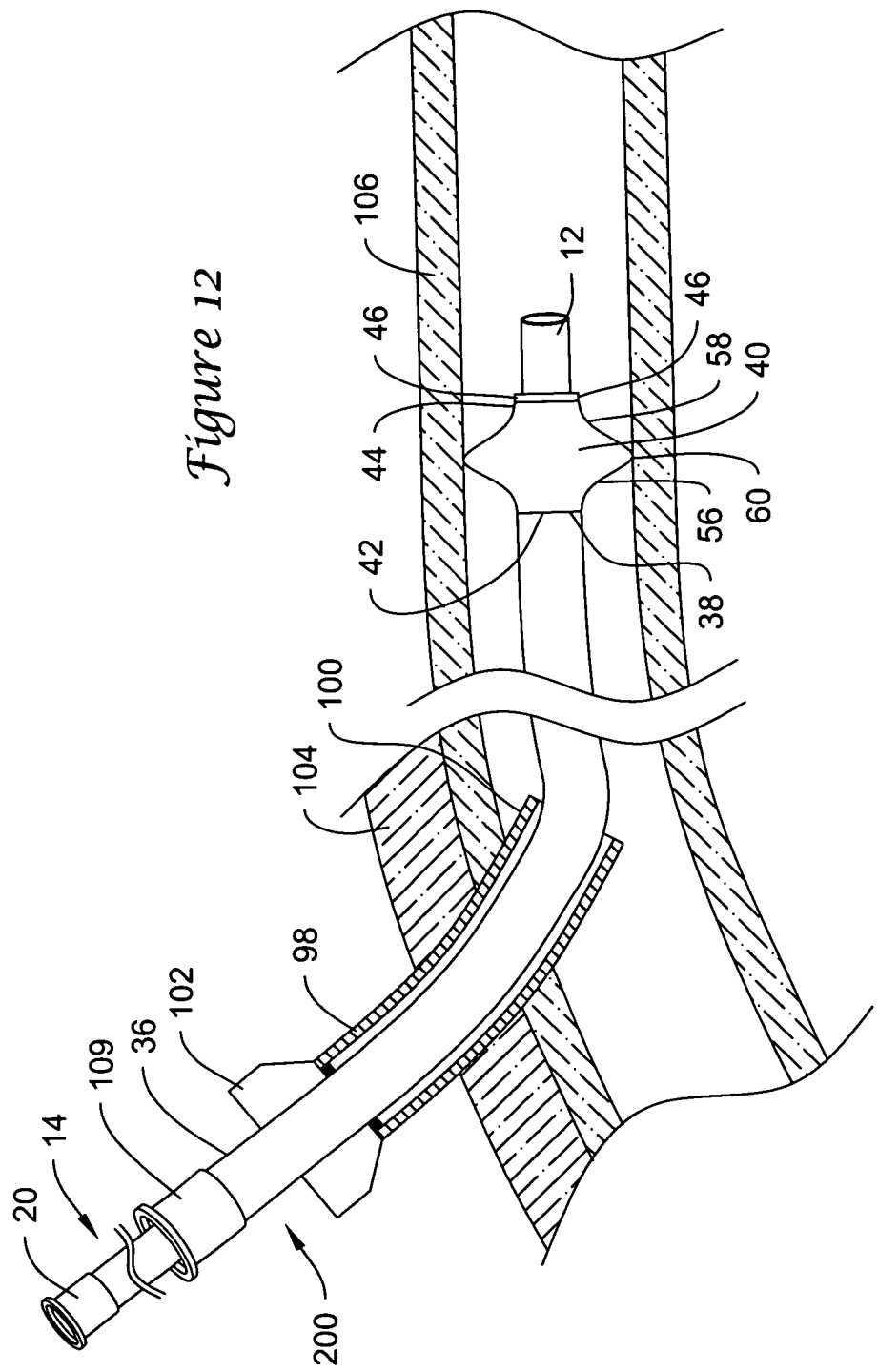
FIG. 12 is a partially-sectioned view of the catheter of FIG. 3, shown advanced into a patient's vasculature, the expandable member shown in its expanded configuration.
Figure 13:
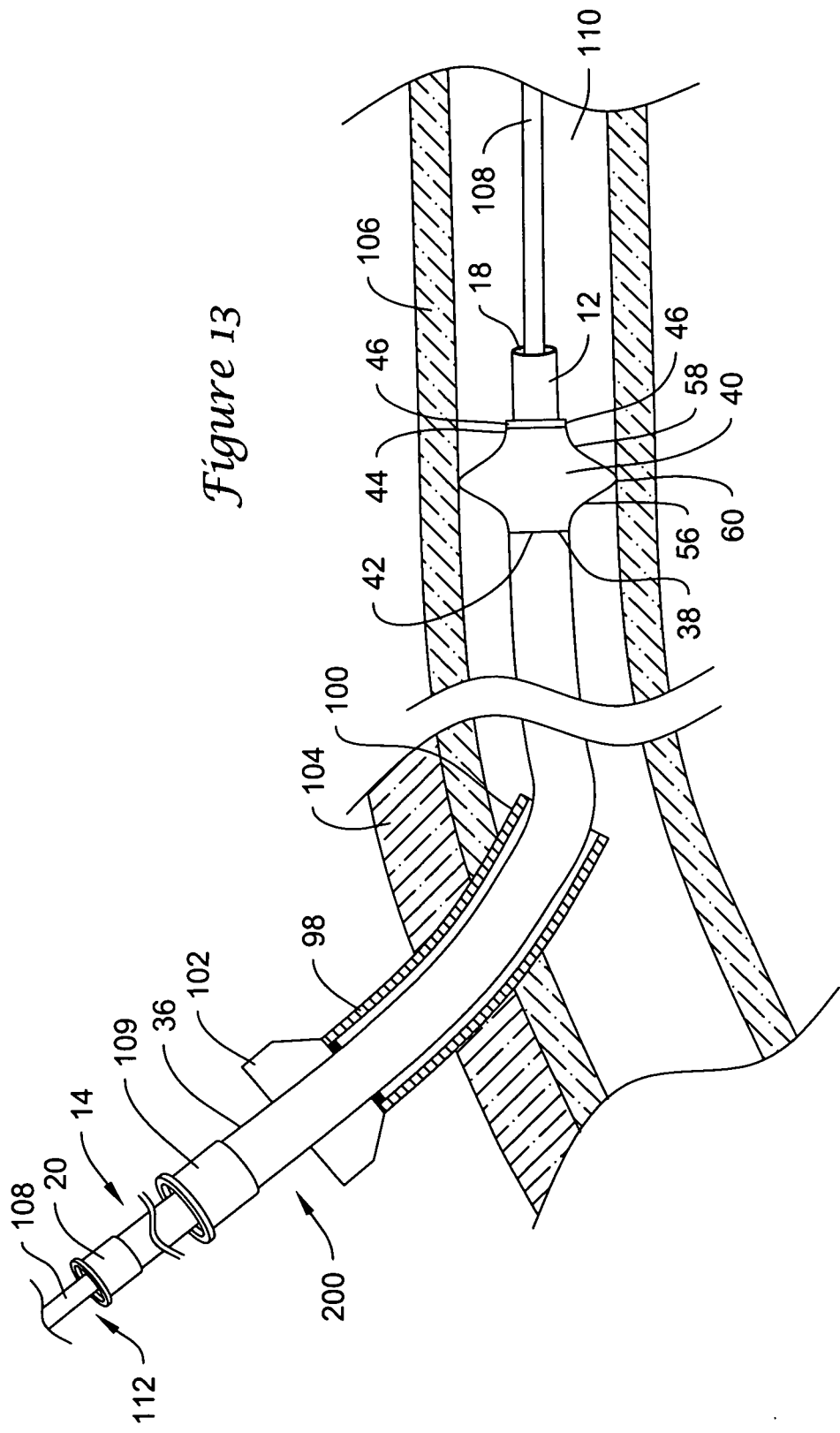
FIG. 13 is a partially-sectioned view of the catheter of FIG. 3, shown advanced into a patient's vasculature, the expandable member shown in its expanded configuration, with a treatment device deployed through the catheter and extending distally of the occlusion.

FIGS. 11-13 demonstrate an intended use of the catheter assembly 200. In FIG. 11, an introducer sheath 98 having a distal end 100 and a proximal end 102 has been extended through a patient's tissue 104 into the patient's vasculature 106 as is well known in the art. In FIG. 11, the catheter assembly 200 has been inserted into the proximal end 102 of the introducer sheath 98 and has been advanced toward a desired treatment site.

As discussed previously, the catheter assembly 200 includes an elongate shaft 12 which extends through the outer member 36 and expandable member 40. As illustrated, the outer member 36 can include a proximal hub 109 that can be configured to easily permit insertion of the elongate shaft 12 therethrough, as well as allowing a physician or other medical professional using the catheter assembly 200 to easily grasp and manipulate the outer member 36.

FIG. 11 shows the catheter assembly 200 with the expandable member 40 in its collapsed configuration. In FIG. 12, however, the expandable member 40 has been moved into its expanded configuration. By comparing FIG. 11 to FIG. 12, it can be seen that in FIG. 12, the outer member 36 has been moved distally relative to its starting position in FIG. 11. As discussed previously with respect to FIG. 5, at least the intermediate portion 60 of the expandable member 40 has moved radially outward and is in at least partial contact with the vasculature 106.

At this point, the catheter assembly 200 is configured for passage of a treatment device such as a balloon catheter, stent delivery catheter, atherectomy device or the like. FIG. 13 illustrates placement of a treatment device 108 having a distal region 110 that extends distally beyond the distal end 18 of the elongate shaft 12 and a proximal region 112 that extends proximally beyond the hub 20 of the elongate shaft 12.

In some embodiments, the treatment device 108 can be positioned within the catheter assembly 200 after moving the expandable member 40 into its expanded configuration, as illustrated. In other embodiments, it can be advantageous to position the treatment device 108 within the catheter assembly 200 prior to expanding the expandable member 40 in order to minimize the amount of time over which blood flow is occluded.

In some embodiments, parts of the catheter assembly 200 can be made of, include, be doped with, include a layer of, or otherwise include a radiopaque material. Radiopaque materials are understood to be materials capable of producing a relatively bright image on a fluoroscopy screen or another imaging technique during a medical procedure. This relatively bright image aids the user of device in determining its location. Some examples of radiopaque materials can include, but are not limited to, gold, platinum, palladium, tantalum, tungsten alloy, plastic material loaded with a radiopaque filler, and the like.

In some embodiments, a degree of MRI compatibility can be imparted. For example, to enhance compatibility with Magnetic Resonance Imaging (MRI) machines, it may be desirable to make any metallic parts such as the cylindrical member 62 in a manner that would impart a degree of MRI compatibility. For example, the cylindrical member 62 can be made of a material that does not substantially distort the image and create substantial artifacts (artifacts are gaps in the image). Certain ferromagnetic materials, for example, may not be suitable because they may create artifacts in an MRI image. The cylindrical member 62 can also be made from a material that the MRI machine can image. Some materials that exhibit these characteristics include, for example, tungsten, Elgiloy, MP35N, nitinol, and the like, and others.

In some embodiments, part or all of the catheter assembly 200 can include a lubricious coating. Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding and solubility. In some embodiments, a distal portion of the catheter can be coated with a hydrophilic polymer, while the more proximal portions can be coated with a fluoropolymer.

It should be understood that this disclosure is, in many respects, only illustrative. Changes may be made in details, particularly in matters of shape, size and arrangement of steps, without exceeding the scope of the invention. The invention's scope is, of course, defined in the language in which the appended claims are expressed.

What we claim is:

1. A catheter having a distal region and a proximal region, comprising:
    an elongate shaft extending from the distal region to the proximal region and defining a lumen therebetween;
    means for occluding a body vessel disposed over a portion of the distal region of the elongate shaft, the means for occluding the body vessel being longitudinally translatable along the elongate shaft and being unsecured to the elongate shaft; and
    means for activating the means for occluding the body vessel disposed over the elongate shaft,
    wherein the means for occluding the body vessel is reversibly movable between a first position in which the means for occluding the body vessel has a first length and a second position in which the means for occluding the body vessel has a second length that is less than the first length,
    wherein the means for occluding the body vessel bas a first diameter at the first position and a second diameter at the second position, where the second diameter is greater than the first diameter,
    wherein the means for occluding the body vessel comprises a distal portion, a proximal portion and an intermediate portion, and the means for occluding the body vessel is configured such that at least the intermediate portion is displaced radially outwardly when moving from the first position to the second position, and
    wherein the means for occluding the body vessel is configured such that the distal portion of the means for occluding the body vessel rotates with respect to the proximal portion of the means for occluding the body vessel in moving from the first position to the second position.

2. A guide catheter assembly having a distal region and a proximal region, the guide catheter assembly comprising:
    an elongate shaft extending from the distal region to the proximal region and defining a lumen therebetween, the elongate shaft having an outer surface;
    an outer member slidably disposed over the outer surface of the elongate shaft, the outer member having a distal end and a proximal region;
    an expandable member having a distal region including a distal end and a proximal region including a proximal end, the expandable member disposed over the outer surface of the elongate shaft such that the distal end of the outer member is proximate the proximal end of the expandable member, and in an unexpanded state, the expandable member being longitudinally translatable along the shaft and being unsecured to the elongate shaft, wherein the expandable member is configured to have a first length in the unexpanded state and a second length in an expanded state, wherein the second length is less than the first length; and
    a stop disposed on the elongate shaft positioned to limit distal travel of the expandable member, where the distal end of the expandable member contacts the stop,
    wherein the expandable member comprises a cylinder and an elastomeric sheath disposed over the cylinder, and
    wherein the expandable member includes a plurality of spirally oriented slits.

3. The guide catheter assembly of claim 2, wherein at least some of the spirally oriented slits extend from the distal region of the expandable member to the proximal region of the expandable member.

4. The guide catheter assembly of claim 2, wherein at least some of the spirally oriented slits extend from the distal end of the expandable member to the proximal end of the expandable member.

* * * * *